United States Patent
Madsen et al.

(10) Patent No.: US 10,327,656 B2
(45) Date of Patent: Jun. 25, 2019

(54) ANALYSIS OF EEG SIGNALS TO DETECT HYPOGLYCAEMIA

(75) Inventors: Rasmus Elsborg Madsen, Kgs. Lyngby (DK); Rasmus Stig Jensen, Kgs. Lyngby (DK)

(73) Assignee: UNEEG MEDICAL A/S, Lynge (DK)

( * ) Notice: Subject to any disclaimer, the term of this patent is extended or adjusted under 35 U.S.C. 154(b) by 1022 days.

(21) Appl. No.: 13/989,304

(22) PCT Filed: Nov. 23, 2011

(86) PCT No.: PCT/EP2011/070843
§ 371 (c)(1),
(2), (4) Date: Jun. 24, 2013

(87) PCT Pub. No.: WO2012/069549
PCT Pub. Date: May 31, 2012

(65) Prior Publication Data
US 2013/0274580 A1    Oct. 17, 2013

(30) Foreign Application Priority Data
Nov. 26, 2010   (GB) .................................. 1020086.3

(51) Int. Cl.
*A61B 5/048*    (2006.01)
*A61B 5/04*     (2006.01)
(Continued)

(52) U.S. Cl.
CPC .......... *A61B 5/04014* (2013.01); *A61B 5/048* (2013.01); *A61B 5/04018* (2013.01);
(Continued)

(58) Field of Classification Search
None
See application file for complete search history.

(56) References Cited

U.S. PATENT DOCUMENTS 3,863,625 A * 2/1975 Viglione .............. A61B 5/4094
                                              600/545
5,146,414 A * 9/1992 McKown ............... A61B 5/026
                                              600/526
(Continued)

FOREIGN PATENT DOCUMENTS

WO   2007/093010 A1   8/2007
WO   2007/144307 A2   12/2007
(Continued)

OTHER PUBLICATIONS

Isaksson, Anders, Arne Wennberg, and Lars H. Zetterberg. "Computer analysis of EEG signals with parametric models." (1981), Proceedings of the IEEE 69.4: 451-461.*
(Continued)

*Primary Examiner* — Navin Natnithithadha
*Assistant Examiner* — Jairo H Portillo
(74) *Attorney, Agent, or Firm* — Sughrue Mion, PLLC

(57) ABSTRACT

Apparatus for detecting hypoglycemia or impending hypoglycemia by analysis of an EEG comprises at least one EEG measuring electrode (10) for gathering an EEG signal and a computer (12) for receiving said EEG signals programmed to obtain a plurality of signal components each comprising a different band of frequencies, obtain a measure of the varying intensity of each said component, obtain a long time estimate of the mean of each intensity measure, obtain a long time estimate of the variability of each intensity measure, normalise each intensity measure e.g. by a subtracting from the intensity measure the long time estimate of the mean and dividing the result by the long time estimate of the variability so as to generate from each band a normalised feature, use machine analysis of the normalised features to obtain a varying cost function, classify values of the cost function according to the probability of the cost function being indicative of hypoglycemia, integrate the probabilities
(Continued)

obtained during a selected time period, and determine that the EEG signals are indicative of hypoglycemia being present or being impending based on said integration.

20 Claims, 6 Drawing Sheets

(51) Int. Cl.
*G06K 9/00* (2006.01)
*A61B 5/00* (2006.01)
*A61B 5/0478* (2006.01)
*A61B 5/145* (2006.01)

(52) U.S. Cl.
CPC ........ *A61B 5/0478* (2013.01); *A61B 5/14532* (2013.01); *A61B 5/7264* (2013.01); *G06K 9/00496* (2013.01); *A61B 5/7267* (2013.01)

(56) References Cited

U.S. PATENT DOCUMENTS

| | | | | |
|---|---|---|---|---|
| 5,813,993 | A * | 9/1998 | Kaplan | A61B 5/0476 600/26 |
| 6,371,923 | B1 * | 4/2002 | Roteliuk | A61B 5/028 600/526 |
| 6,572,542 | B1 | 6/2003 | Houben et al. | |
| 2001/0037070 | A1 * | 11/2001 | Cranley | A61B 5/00 600/532 |
| 2006/0036153 | A1 * | 2/2006 | Laken | A61B 5/0476 600/410 |
| 2006/0111644 | A1 * | 5/2006 | Guttag | A61B 5/048 600/544 |
| 2007/0219455 | A1 * | 9/2007 | Wong | A61B 5/02405 600/515 |
| 2009/0006061 | A1 * | 1/2009 | Thukral | G06F 19/325 703/11 |
| 2009/0007918 | A1 | 1/2009 | Darkin et al. | |
| 2009/0024050 | A1 * | 1/2009 | Jung | A61B 5/16 600/544 |
| 2009/0287107 | A1 | 11/2009 | Beck-Nielsen et al. | |
| 2011/0077484 | A1 * | 3/2011 | Van Slyke | A61B 5/02416 600/324 |

FOREIGN PATENT DOCUMENTS

| | | | | |
|---|---|---|---|---|
| WO | WO 2010041197 A1 * | 4/2010 | | G06F 19/3431 |
| WO | 2010/121301 A1 | 10/2010 | | |
| WO | 2011/070843 A1 | 11/2010 | | |

OTHER PUBLICATIONS

Scott Makeig et al "Changes in Alertness are a Principal Component of Variance in the EEG Spectrum" NeuroReport 7:213-217 (1995) pp. 1-7.
J. Gade et al, "Detection of EEG Patterns Related to Nocturnal Hypoglycemia" Methods of Information in Medicine 1994; 33 pp. 153-156.
Ernst Haselsteiner et al, "Using Time-Dependent Neural Networks for EEG Classification", IEEE Transactions on Rehabilitation Engineering, vol. 8, No. 4, Dec. 2000, pp. 457-463.
International Search Report for PCT/EP2011/070843 dated Feb. 3, 2012.

* cited by examiner

ANALYSIS OF EEG SIGNALS TO DETECT HYPOGLYCAEMIA

CROSS REFERENCE TO RELATED APPLICATIONS

This application is a National Stage of International Application No. PCT/EP2011/070843, filed on Nov. 23, 2011, claiming priority from British Patent Application No. 1020086.3, filed Nov. 26, 2010, the contents of all of which are incorporated herein by reference in their entirety.

The invention relates to a method of predicting and warning of hypoglycemic attacks for people such as but not limited to diabetics. Moreover the invention relates a device for prediction and warning of hypoglycemic attacks for people such as but not limited to diabetics.

Hypoglycemic attacks occur as a result of a too low blood sugar concentration, which is mostly a problem for diabetics, who are treated with insulin or other blood sugar regulating medical drugs. Others at risk include those having a genetic predisposition to having a low blood sugar. The attacks can be highly severe and often entail unconsciousness. The risk of an attack therefore often limits the possible activities of the people concerned, which furthermore reduces their quality of life. Attacks can be prevented in a simple way, e.g. by consuming appropriate food when glucose values become critical. The problem is however that many in the risk group cannot by themselves sense when their blood sugar concentration reaches a critically low level with risk of an attack. The number of people in the risk group is approximately 10 million.

The level of blood glucose low enough to cause hypoglycemia may be different for different people, in different circumstances, and for different purposes, and occasionally has been a matter of controversy. Most healthy adults maintain fasting glucose levels above 70 mg/dL (3.9 mmol/L), and develop symptoms of hypoglycemia when the glucose falls below 55 mg/dL (3 mmol/L).

Neuroglycopenia refers to a shortage of glucose (glycopenia) in the brain, usually due to hypoglycemia. Glycopenia affects the function of neurons, and alters brain function and behaviour and causes changes in the EEG. Prolonged neuroglycopenia can result in permanent damage to the brain.

There are known methods and devices for prediction of hypoglycemic attacks.

In U.S. Pat. No. 6,572,542 a method and a device are described, which among others have the purpose of warning of hypoglycemic attacks. This uses a combination of EEG measurements to indicate an individual's blood glucose level and the individual's ECG (electrocardiographic) signals to indicate the rate of change of blood sugar concentration as inputs to an artificial neural network learning processor, from which is obtained a signal that is used for alerting the user or to control administration of a therapeutic material.

However, no specific method of obtaining or analysing EEG signals is described and nor are any results of practising the described methods given.

Gade J., Rosenfalck A. and Bendtson I., Meth Inform Med 1994; 33: 153-6 investigates the possibility of providing a patient hypoglycemia alarm and describes the detection of EEG patterns related to nocturnal hypoglycemia. EEG signals from bipolar EEG surface electrodes C4-A1 and C3-A2 are digitised offline and are divided into 2 second time segments. Amplitude and spectral content from these is fed to a Bayes probabilistic classifier of undisclosed type which is trained according to an unsupervised learning process. The rate of occurrence of events classified as indicative of hypoglycemia is observed. It is concluded that inter-patient variability does not allow for the construction of a common learning set for all patients and that construction of a personal learning set will be required for all patients.

In WO 2007/144307, we provided an algorithm for application to a patient's EEG to detect therein patterns indicative of hypoglycemic events taking account of a finding that in order to obtain sufficient specificity and sensitivity of detection of EEG changes indicative of the onset of hypoglycemia, it is not sufficient to consider only the occurrence of such changes nor the rate at which they occur. Otherwise, sporadic EEG events consistent with hypoglycemia or temporary bursts of such events can lead to a false alarm being triggered. The present invention provides an improved procedure for such EEG analysis.

According to the present invention there is now provided a computer based method for detecting hypoglycemia or impending hypoglycemia by analysis of an EEG (or for determining whether an observed EEG is compatible with a state of hypoglycemia or impending hypoglycemia) comprising inputting an EEG signal to a computer, in said computer obtaining from said signal a plurality of components thereof each component comprising a different band of frequencies and obtaining a measure of the varying intensity of each said component, obtaining a long time estimate of the mean of each said intensity measure, obtaining a long time estimate of the variability of each said intensity measure, normalising each said intensity measure by a process arithmetically equivalent to subtracting from the intensity measure the long time estimate of the mean and dividing the result by the long time estimate of the variability so as to generate from each band a normalised feature, using machine analysis of the normalised features to obtain a varying cost function, classifying values of each said cost function according to the probability of said cost function being indicative of hypoglycemia, integrating the probabilities obtained during a selected time period, and determining in said computer that the EEG signals are indicative of hypoglycemia being present or being impending based on said integration.

In accordance with the present invention, the detection of hypoglycemia or impending hypoglycemia may be conducted by detecting EEG signal patterns that are associated with a blood glucose level at or below a threshold value, e.g. a threshold of 3.5 mmol/l. The intensity measure or measure of the size of the signal is preferably the absolute value of the signal, i.e. the 1 norm $$\|f\|_1 = \sum_{-\infty}^{\infty} |f(t)| dt.$$

However, other intensity measures may be employed such as the 2-norm $$\|f\|_2 = \left(\sum_{-\infty}^{\infty} |f(t)|^2 dt\right)^{1/2}.$$

It may be the area under the curve of the squared signal per unit time. Generally it may be any length measure on the filtered signal, whether the absolute value, squared values or another distance measure.

The estimate of the variability of a measure herein may be an estimate of the variance thereof. An estimate of the variance of a parameter, whether the parameter is an intensity measure or is a cost function, may be based on the reciprocal of an upper percentile of the parameter, for instance a percentile in the range of $75^{th}$ to $85^{th}$ percentile.

A 'long time estimate of the mean' of a parameter (whether the parameter is an intensity measure or is a cost function) is an estimate of the mean of measurements of the parameter taken frequently over a long period which is preferably at least 3 hours, more preferably at least 6 hours, more preferably at least 9 hours or more preferably at least 12 hours. The frequency of measurement is preferably on average at least one per minute, more preferably at least 30 per minute, more preferably one per second.

A 'long time estimate of the mean' of a parameter (synonymous with "long term estimate of the mean, and whether the parameter is an intensity measure or is a cost function) is an estimate of the mean of measurements of the parameter taken frequently over a long period which is preferably at least 3 hours, more preferably at least 6 hours, more preferably at least 9 hours or more preferably at least 12 hours. The frequency of measurement is preferably on average at least one per minute, more preferably at least 30 per minute, more preferably one per second. In order that a meaningful long time estimate is available as soon as use of the method or apparatus of the invention starts, it is preferable that means is provided for storing in memory a corresponding long time estimate for each value needed which was obtained in a previous session of use, and that previous session estimate is used at the start of a current session and is progressively updated as the current session progresses. Means is preferably provided for storing all long time estimates in use at the end of a session of EEG monitoring, or as described below, switching from the use of one algorithm to use of another.

The estimate of the variance of a parameter may be calculated as the value obtained from a long time estimate of the mean of said upper percentile value p less the long time estimate of the mean of the parameter m, i.e. (p−m) or any arithmetical equivalent. The normalisation X of a raw signal x is then obtained as X=(x−m)/(p−m).

The machine analysis of the normalised features is preferably conducted using analytical parameters, e.g. said weighting coefficients, which are generally applicable across a population of individuals and which are not special to the person from whom the EEG under analysis is derived.

In a method according to the invention said cost function may be obtained as a sum of a linear or non-linear function of the normalised features using a pre-established set of weighting coefficients.

Each said time segment cost function may be classified as being an event indicative of hypoglycemia or as being not an event indicative of hypoglycemia, and said integration of probabilities is carried out by integrating the number of events detected during said selected time period.

The method may further comprise estimating the long time variability of the cost function, and normalising the cost function by a process arithmetically equivalent to subtracting from the cost function the long time estimate of the mean and dividing the result by the long time estimate of the variability so as to generate the normalised cost function and wherein it is said normalised cost function which is classified in said classifying step.

The method may further comprise detecting time segments of said EEG which contain signal contaminating artifacts confusable with hypoglycemia patterns and excluding said time segments from generating events to be included in said integration.

Said time segments of said EEG which contain signal contaminating artifacts may be identified by obtaining a sum of a linear or non-linear function of the normalised features using a pre-established set of weighting coefficients to obtain a varying artifact detection cost function, and classifying each said artifact detection cost function according to the probability of said artifact detection cost function being indicative of a said artifact.

The classification may be binary so that the cost function is classified as either being indicative of an artifact or as not being indicative of an artifact.

The method may further comprise estimating a long time mean of the artifact detection cost function, estimating the long time variability of the artifact detection cost function, and normalising the artifact detection cost function by a process arithmetically equivalent to subtracting from the artifact detection cost function the long time estimate of the mean and dividing the result by the long time estimate of the variability so as to generate the normalised artifact detection cost function and wherein it is said normalised artifact detection cost function which is classified in said classifying step.

The classification is preferably conducted by a process of machine analysis and the machine analysis of the normalised features is preferably conducted using analytical parameters which are generally applicable across a population of individuals and which are not special to the person from whom the EEG under analysis is derived.

Optionally, said EEG signal is divided into a sequence of time segments and said measure of the intensities of said components is obtained for each time segment. Further, said values of said cost function which are classified may be values thereof for each of said time segments. Said integration is optionally carried out over a selected number of preceding time segments which together constitute said selected time period.

Generally, the EEG signal will at the outset be digitised and sampled prior to further processing.

The EEG signal may be filtered to provide said components using a digital filter and depending on how this is conducted, this may involve division of said signal into said time segments, for instance if the filtering is performed using an FIR filter. However, it is considered preferable not to divide the signal into time segments.

It may be noted that the step of dividing said EEG signal into a sequence of time segments and obtaining from said signal a plurality of components thereof having a different band of frequencies is not intended to be limited to performing the task of division into time segments before obtaining said plurality of components. Depending on the techniques used, the separation into bands can come before the division into time segments. Either way, one obtains division both into bands of different frequencies and into time segments.

The invention further provides a computer programmed to accept an EEG signal as an input and to perform thereon the steps of obtaining from said signal a plurality of components thereof each component comprising a different band of frequencies, and obtaining a measure of the varying intensity of each said component, obtaining a long time estimate of the mean of each said intensity measure, obtaining a long time estimate of the variability of each said intensity measure, normalising each said intensity measure by a process arithmetically equivalent to subtracting from the intensity measure the long time estimate of the mean and dividing the result by the long time estimate of the variability so as to generate from each band a normalised feature, using machine analysis of the normalised features to obtain a varying cost function, classifying values of said cost function according to the probability of said cost function being indicative of hypoglycemia, integrating the probabilities obtained during a selected time period, and determining in said computer that the EEG signals are indicative of hypoglycemia being present or being impending based on said integration.

The computer may be open to receiving programming or may be wholly or partially constituted by firmware in which the requisite programming is hardwired.

The invention further provides a machine instruction set containing instructions for causing a compatible computer to carry out the step of receiving as an input an EEG signal and to perform thereon the steps of obtaining from said signal a plurality of components thereof each comprising a different band of frequencies, and obtaining a measure of the varying intensity of each said component, obtaining a long time estimate of the mean of each said intensity measure, obtaining a long time estimate of the variability of each said intensity measure, normalising each said intensity measure by a process arithmetically equivalent to subtracting from the intensity measure the long time estimate of the mean and dividing the result by the long time estimate of the variability so as to generate from each band a normalised feature, using machine analysis of the normalised features to obtain a varying cost function, classifying values of said cost function according to the probability of said cost function being indicative of hypoglycemia, integrating the probabilities obtained during a selected time period, and determining in said computer that the EEG signals are indicative of hypoglycemia being present or being impending based on said integration.

The invention further provides apparatus for use in providing warning of hypoglycemia or impending hypoglycemia comprising EEG gathering electrodes and a suitably programmed computer for carrying out the method of the invention.

All of the features or characteristics of the invention described in relation to the method of the invention may be employed in the programmed computer or instruction set/computer program of the invention, which may be encoded on a machine readable carrier or memory.

The invention will be further described and illustrated with reference to the accompanying drawings in which.

We shall describe a preferred embodiment of the invention in which a single channel EEG signal is processed for detection of hypoglycemia. However, the scheme described below is easily modified to use multiple electrodes to gather EEG signals. When using multiple electrodes, one can average their signals to obtain more robust evidence. Alternatively, one can use inconsistency in their signals to identify the presence of artifacts such as EMG artifacts by the use of Independent Component Analysis (ICA) or other machine learning methods. Such a single channel EEG signal can be obtained from a single EEG measuring electrode and one ground or reference electrode, shown schematically in FIG. 1 as block 10. These may be positioned on the scalp of the patient or more preferably may be implanted beneath the scalp outside the skull. As an alternative to subcutaneous implantation, they may be implanted beneath the skull. When outside the skull at least, preferred positions for the electrodes will be such as (P4-T6), (P4-T4), (P3-T5), or (P3-T3) in the standard EEG 10-20 system (see WO2007/144307). Alternatively or additionally, electrodes may be situated in the ear canal.

The use of multiple electrode positions spaced along a straight or curved line facilitates the use of implanted electrodes as the conductors connecting thereto may be all led out in the same direction along a common path.

The electrode or electrodes 10 produce a continuous stream of signals which are applied as an input to a computer 12 providing a signal processing unit from which is output a signal indicating whether the patient is or is not in a hypoglycemic condition based upon the EEG signals.

The signal processing unit may physically be split into two or more units and in particular into an internally implanted unit and an external (of the body) unit such that some initial signal processing is performed in the implanted unit and the processed signals are transmitted from the implanted unit to the external unit for further processing leading to the eventual production of the output signal indicating whether the patient is or is not in a hypoglycemic condition based upon the EEG signals.

In a first phase of processing, the EEG signals are digitized and sampled to provide 64 samples per second with a signal dynamic range of 12 bit and one LSB (least significant bit) set at 1 µV.

Figure 1:
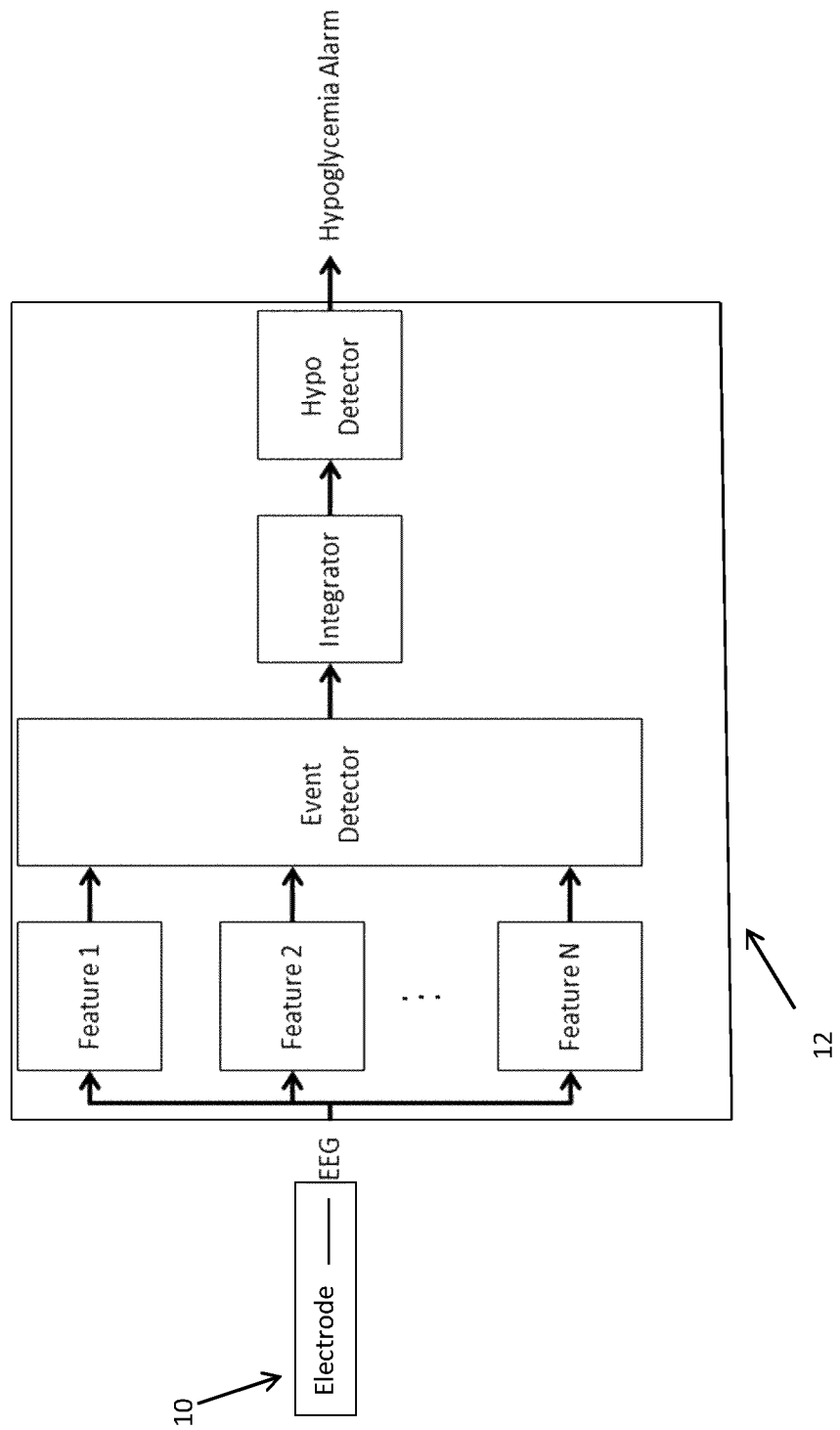
FIG. 1 shows schematically the structure of apparatus according to the invention and the EEG signal processing algorithm used therein.

A signal processing algorithm is applied which is built from four blocks as shown in FIG. 1. The first block is fed with the 64 Hz sampled EEG data stream and converts this stream to a 1 Hz feature vector stream.

The feature vectors are each fed to an event detector (classifier), which determines if the vector has a pattern that is associated with impending hypoglycemia. The event detector classifies a feature vector to a single binary value, 1 (hypo) and 0 (normal). The binary event stream is integrated in the integrator block to a number that reflects the number of events that has occurred during the past X seconds. If the output of the Integrator exceeds a certain threshold, the Hypo Detector block emits an alarm. The alarm emitted by the Hypo Detector block may activate an alarm signal generator to output a physically perceivable alarm signal such as a sound or vibration or mild electrical shock perceivable by a user of said apparatus. Alternatively or additionally the alarm signal may be communicated to a remote monitoring station.

These component blocks of the algorithm are described in more detail as follows.

Feature Extraction and Normalization

Figure 2:
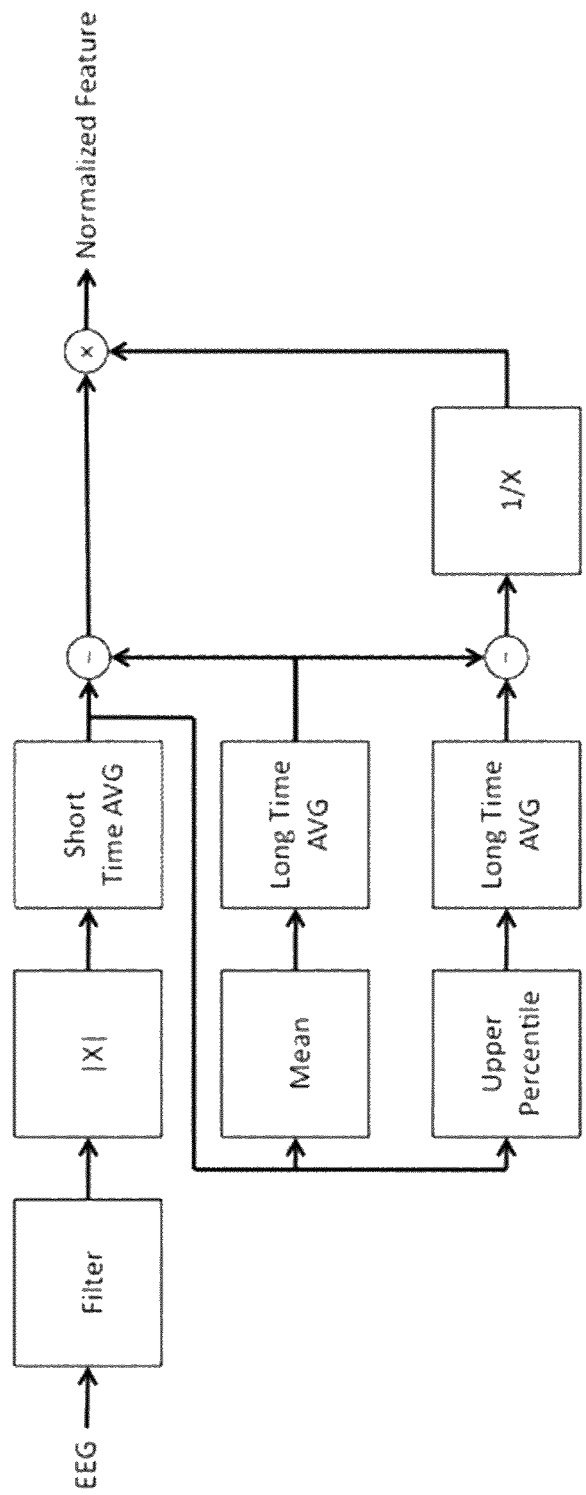
FIG. 2 shows detail of the 'Feature' blocks of FIG. 1.

The feature extraction and normalization functionality is shown in FIG. 2. Each feature normalization block (1:N) (in FIG. 1) receives the full EEG stream. There is a filter in each feature block that extracts specific characteristics of the EEG. The filtering can be carried out by various filter configurations, e.g. FIR or IIR filter structures of different orders. In this embodiment, there are N=9 feature blocks, where the filters are pass-band filters with 3 dB pass-bands (1.0 Hz-2.5 Hz; 2.5 Hz-4.0 Hz; 4.0 Hz-5.0 Hz; 5.0 Hz-6.0 Hz; 6.0 Hz-7.0 Hz; 7.0 Hz-8.0 Hz; 8.0 Hz-10.0 Hz; 10.0 Hz-12.0 Hz; 12.0 Hz-20.0 Hz). The filter coefficients for each feature block are therefore different from the other blocks.

The structure of the feature estimation and normalization as applied to each feature is shown in FIG. 2.

In a block labelled (|X|), the absolute value (1-norm) of the filtered signal is calculated, which is then optionally accumulated over one second in a Short Time AVG block. Alternatively, the Short Time AVG block can be omitted. The data-rate is also reduced to 1 Hz in this Short Time AVG block if present. The absolute value or the output of the Short Time AVG block is named raw-feature.

Instead of the 1-norm, one could use any other intensity measure as described above. A long time estimate of the mean is calculated as the $50^{th}$ percentile of the raw-feature, which is averaged over time in a "Long Time AVG" block. A long time estimate of the variance is calculated by averaging the $80^{th}$ percentile (upper percentile) of the raw-feature, in a respective "Long Time AVG" block. The estimate of the mean is then subtracted from the long time estimate of the upper percentile to get an estimate of the reciprocal of the variance 'x'. The raw-feature is normalized by first subtracting the estimate of the mean (long time estimate) and then by dividing by the estimate of the variance.

This is done in the same way for each feature, so producing N normalised features.

Alternatively, one may use an FFT or similar transform, in which case the time segmentation (if performed) would happen prior to splitting of the signal into components of differing frequency, i.e. the reverse order to that involved in the method described in detail above.

Event Classification and Artifact Removal

Figure 3:
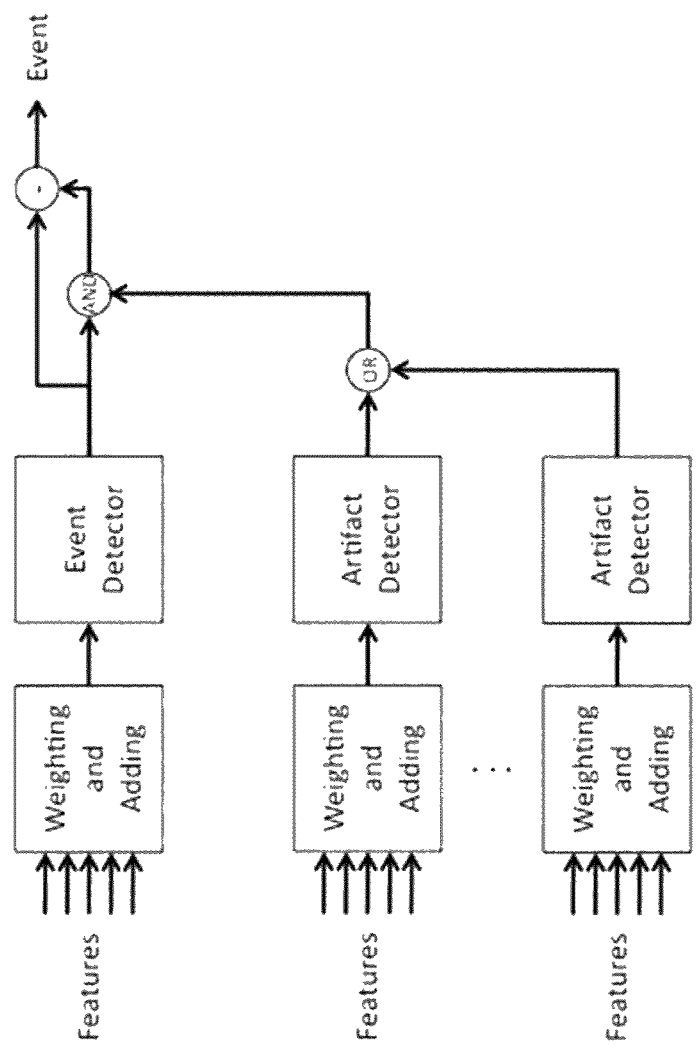
FIG. 3 shows detail of the 'Event Detection' block of FIG. 1.

FIG. 3 shows a hypoglycemia event classifier together with two optional artifact detectors. The hypoglycemia event classifier and artifact classifiers, all have the same structure, which accepts as input in each case the N normalized features, which are inputs to each of the structure.

In the Event Classifier, the normalized features are first weighted by a first set of coefficients and then added together giving a cost function which is output from the module marked 'Weighting and Adding' to the module marked 'Event Detector'. The derivation of the first set of coefficients will be described later below.

Each artifact detector is similarly structured and receives the same normalised features as inputs, applies a respective second or third set of weighting coefficients (to be described below) and adds the weighted normalised features to produce a respective separate cost function which is passed to the respective Artefact Detector module. There is thus one cost function for the event-detector and two separate cost functions for detection of artifact signals, but there could be more. The cost functions supply the input to the detector blocks in FIG. 3. Each of these has the structure shown in FIG. 4.

This form of Event Classifier or artifact detector can be considered to be an approximation of an artificial neural network (ANN) as although the classifiers operate as linear classifiers, some non-linearity is derived from the fact that the fixed point number format used only has a limited dynamic range, i.e. when signals run into the upper bound they can get no larger. This effect is similar to the non-linearity of the sigmoid function or tank function used for activation in some ANN. These forms of ANN could of course also be used.

Each detector block first normalizes the cost-function and then determines the event output (by the action of the Detector box in FIG. 4), based on the cost function. In the base implementation, the detector box supplies a binary output, but in another implementation of the event-detector the output can be expressed with more bits.

The artifact detector blocks in FIG. 3 each supply a binary output that is either 0 or 1. The two outputs are put through a logical OR function that outputs a "1" if any of the artifact detectors has found an artifact signal. The output of the OR function is AND'ed with the output of the "Event Detector", and the output of this logical function is then extracted from "Event Detector" output. The functionality of these operations is simply to block the output of a signal indicating the detection of a hypoglycemic event when either of the artifact detectors has detected an artifact. Hypoglycaemia events will therefore only be detected when there are no artifact signals in the EEG (as defined by the weighting and adding scheme in the artifact detectors).

Figure 4:
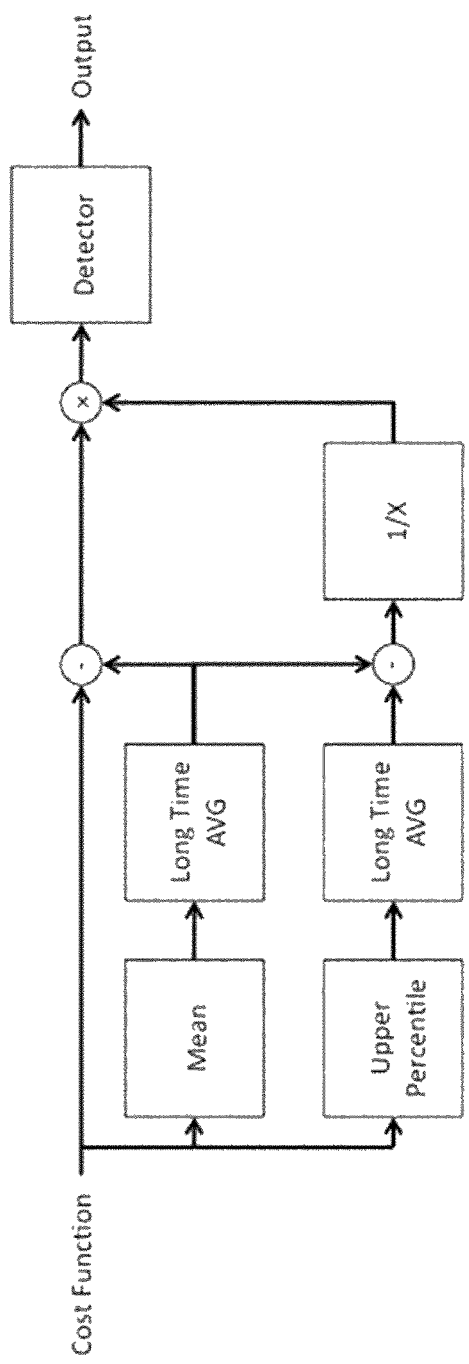
FIG. 4 shows detail of the cost function normalisation optionally employed according to the invention in each 'Detector' block of FIG. 3.

Each of the Event Detector modules of FIG. 3 is as shown in FIG. 4. The cost function received from a Weighting and Adding module in FIG. 3 is normalised as follows. First the module estimates a long time averaged estimate of the mean value of the cost function, which is calculated as the 50 percentile (box marked 'Mean'), which is then averaged by a filter (Long Time AVG). An estimate of the variance is computed as the 80 percentile, which is also averaged over a long time, followed by subtraction of the estimated mean. The estimated mean is subtracted from the cost function, and the result is then divided by the estimated variance, giving the "normalized cost function". The basic implementation of the "Detector" is binary, meaning that the output of the detector is "0" when the input is below a certain threshold and "1" otherwise.

The "Detector" can also be implemented in a more advanced manner, where the output is variable (more than 1 bit). The output is then zero if the input is below a certain threshold, and otherwise a function of the input. The suggested function is: output=(input−const1)*const2+const3. If the advanced implementation is used as the hypoglycemia event detector, the "AND" and "-" in (FIG. 3) should be substituted with a function that sets the event detector output to zero if an artifact event is detected.

Integration of Events

The evidence for hypoglycemia is not strong enough if one only considers a single hypoglycemia event. Noises and artifacts in the EEG can resemble the hypoglycemia EEG pattern and there will therefore be false positive events that are detected by the "Event Classifier". The hypoglycemia pattern will appear repeatedly with higher repetition frequency when hypoglycemia is impending. The evidence from the classifier is therefore integrated (by a digital IIR filter) where the event evidence for past 5 minutes is considered. The integrated evidence gives a robust estimate of the likelihood of hypoglycemia. The filtering method basically sums the evidence for the past 5 minutes.

The standard way of implementing the integration function would be by use of a memory block where the evidence of the last 5 minutes is stored in a circular memory buffer, and summed together every time a sample is updated. When implementing this integration function by an IIR filter, the memory requirements are small and the operations are computationally simpler while it at the same time allows for greater flexibility if the integration function needs to be changed. The IIR filter can be constructed in various ways that generally lead to the same functionality. One suitable implementation of a known type is shown in FIG. 5.

Figure 5:
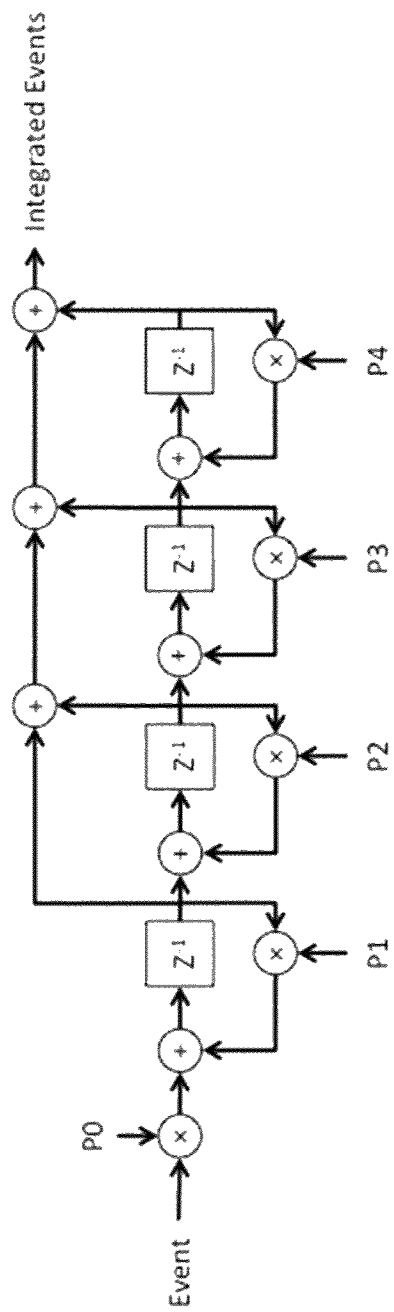
FIG. 5 shows detail of the integration applied to the events which are the output of FIG. 3.

In FIG. 5, P0, P1, P2, P3 and P4 are coefficients. "Event" is a new event (zero or one) that enters the integrator and is multiplied by "P0" and then added together with the feedback from the first delayed signal, where "Z-1" indicates the delay. The data processing is similar in the following blocks. All the stored values (after the "Z-1" blocks) are finally added together, resulting in the "Integrated Events".

Alarm Detection

The alarm detector continuously monitors the output from the integrator block. When the integrated evidence passes a certain threshold, the evidence of impending hypoglycemia is high enough for the unit to emit a hypoglycemia alarm signal.

Since the hypoglycemia EEG pattern will be present until the brain gets enough glucose again, it is likely that the evidence in the integrator will continue to rise during the following minutes until the user manage to normalize his glucose levels. A solution to this problem is to bypass the alarm until the integration evidence has been reduced to level below the alarm threshold or to bypass the alarm for a certain amount of time after the alarm has been given. The latter solution is currently preferred.

Training the Classifier

We indicated above that the normalised Features are subjected to weighting and adding in the "Weighting and adding" blocks in FIG. 3 using respective sets of parameters that determine to what extent each normalised feature should influence the outcome of the event detector and the artifact detectors. These sets of coefficients once obtained can be used generally for all patients. The coefficients are obtained by training signal processing unit in a process of machine learning.

One starts with an arbitrary initial set of coefficients for the event detector of FIG. 3.

On makes use of a dataset which contains EEG from a number of subjects who have been exposed to hypoglycemia. The dataset includes EEG recordings from subjects in norma-glycaemia situations ad well as hypoglycemia situations. Both situations have been recorded during sleep as well as when the subjects are awake. Blood samples have been taken during the time of recording and the plasma-glucose-level has been determined to validate whether the subject was hypoglycemic.

The EEG recordings have been analysed by neurophysiologists, as well as sleep experts who have supplied the recordings with labels of hypoglycemia related EEG-changes and sleep phases.

These EEG recordings are analysed using the above described algorithm. The starting set of parameters is altered to improve the extent to which the algorithm identifies hypoglycemic events in each EEG in agreement with the experts.

Figure 6:
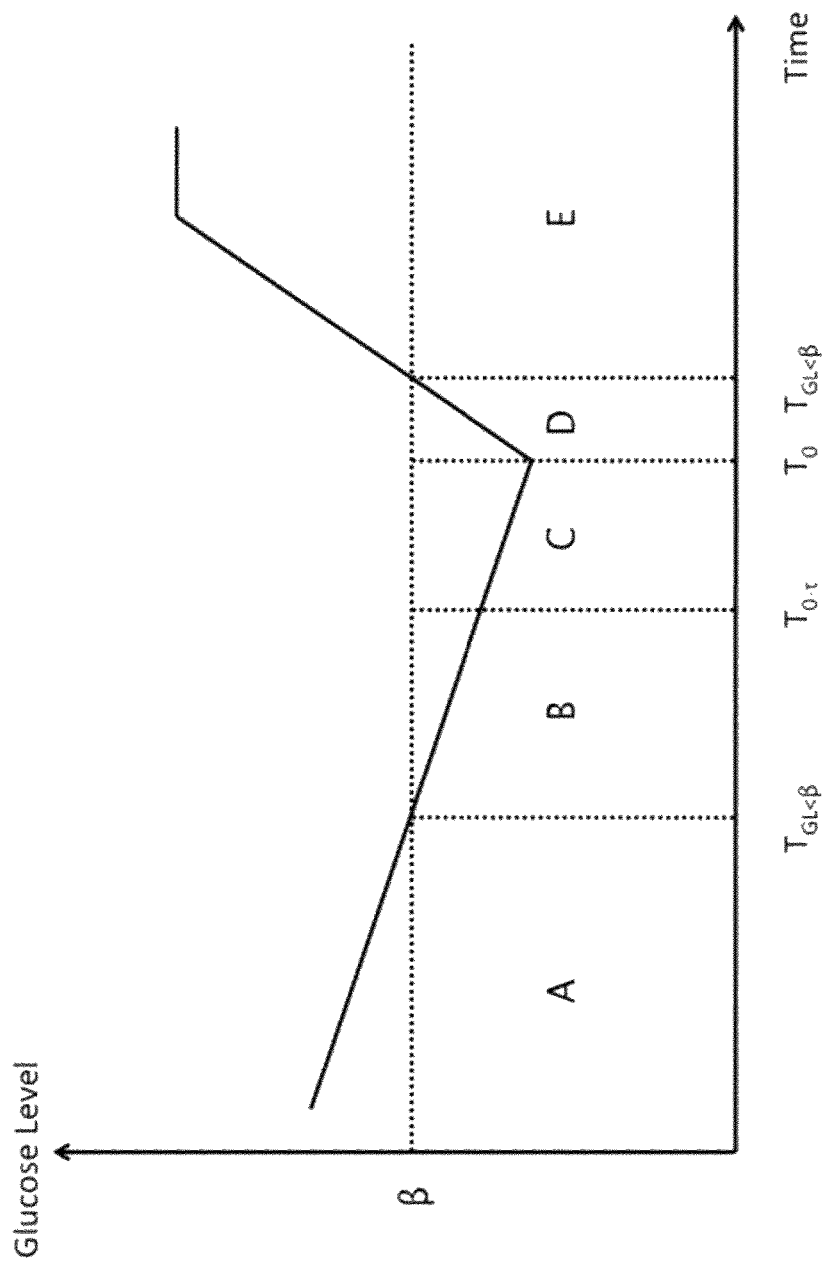
FIG. 6 shows a graph of the time course of blood glucose levels used in generating EEGs for use in training a classifier for use in the 'Weighting and Adding' blocks of FIG. 3.

FIG. 6 shows the time course of a typical EEG recording of this kind and divided into zones A, B, C, D and E. In zone A, the glucose level is above $\beta=3.5$ mmol/l. Accordingly, in this zone of the EEG the algorithm should not detect events. In zone B, a certain number of events may be expected to be found by a properly functioning algorithm as the glucose level falls, but not sufficient events to integrate to an alarm signal. In zone C (defined by being the period of 10 minutes before $T_0$ i.e. the time instant when the glucose level falls to hypoglycemia according to the experiment protocol) more hypoglycemic events should be detected, leading to integration to a level generating an alarm. In zone D, glucose is administered and although there will be hypoglycemic events detected, they will be too contaminated by artifacts to be of value. In zone E, the glucose level is too high for hypoglycemic events to be correctly detected.

A cost function for the output of the event detector is defined as follows:

$$\text{Costfunction} = +(\Sigma_A \text{events}) - (\Sigma_B \text{events}) - (2 \times \Sigma_C \text{events}) + (\Sigma_E \text{events})$$

where $\Sigma_A$events is the number of events detected by the algorithm in time zone A and so forth. The weighting of the events need not necessarily be precisely as shown in this formula, which is indicative rather than limiting.

The starting set of parameters is adjusted to optimise this cost function to bring it into line with the value expected from the expert analysis of the EEG recording.

There are many ways of optimizing this kind of cost function. A suitable method is to calculate the gradient for all the parameters and perform gradient descent with the use of linesearch.

The set of parameters so obtained is of course generally applicable across a population of individuals and the parameters are not special to the person from whom the EEG under analysis is derived.

The respective sets of parameters for the artifact detectors of FIG. 3 are similarly obtained by training. For instance, EEGs may be manually marked up to show features associated with the action of chewing. An artifact detection classifier can then be trained as described above to output an artifact detected signal when such marked up features are encountered. Again, the analytical parameters so obtained are generally applicable across a population of individuals and which are not special to the person from whom the EEG to be analysed is derived.

Other artifact detectors can be trained to recognise other forms of activity that give rise to signals that can be confounded with hypoglycemia. These may include sleep artifacts, as well as other muscle or EMG noise sources.

Night and Day Algorithm

Since the circumstances for night-time and daytime hypoglycemias are different (the EEG is very different at night), it is desirable to train the event detector as described above using daytime EEGs as a training set to develop a first set of event detector feature weighting parameters and to repeat the exercise using night-time EEG recordings to develop a second set of parameters. This provides separate algorithms for use during the day and during the night by patients.

To a degree, the two algorithms work when used with the 'wrong' kind of data (night/day), however with a decreased performance.

In FIG. 2 and FIG. 4, the normalization functionality that normalizes the features and the event classifier cost function, are based on the previously recorded data. Since the data statistics are different for daytime and night-time data, the normalization functionality has a different effect during day and night. It is therefore important that the daytime algorithm is normalized with daytime data statistics and vice versa. Optionally, one may have a first physical device that is used during daytime only, and another device that is used during night-time. Alternatively, one could provide a single device with switching between night time and daytime parameter sets and with an appropriate initial set of normalisation parameters for use in each of its night-time and daytime modes.

Preferably, when switching from one of the night time and day time algorithms to the other, relevant long time estimates are loaded from the previous session of the algorithm to be used.

Physical Structure of the Apparatus

The analysis of the EEG and the generation of any form of alarm signal may, as tasks, be split between an implanted module connected to the EEG electrodes and an external module communicating with the internal module, as described in WO2006/066577 and in WO2009/090110. In order that the internal module can derive sufficient power from continuous supply via internal and external inductive coils it is preferred currently that the internal module should receive the EEG, carry out the analog to digital conversion, reduce the sample rate and filter out unwanted high frequency components and transmit the resulting signal to the external module where all remaining steps are carried out. However, if an implanted power supply such as a rechargeable battery of sufficient capacity were employed more or even all of the functions could be conducted in the implanted module.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A computer based method for detecting hypoglycaemia or impending hypoglycaemia by analysis of an EEG from a wearable EEG monitor, said method comprising:

measuring an EEG signal from a person carrying said EEG monitor;

inputting said EEG signal to a computer;

in said computer, obtaining from said EEG signal a plurality of components thereof, each component comprising a different band of frequencies, and obtaining a measure of the varying intensity of each said component;

obtaining a long term estimate of the mean of each said intensity measure and obtaining a long term estimate of the variability of each said intensity measure;

normalising each said intensity measure by a process arithmetically equivalent to subtracting from the intensity measure the long term estimate of the mean and dividing the result by the long term estimate of the variability so as to generate from each frequency band a normalised feature, using machine analysis of the normalised features to obtain a time-varying hypoglycaemia cost function;

classifying values of said hypoglycaemia cost function according to a probability of the values of said hypoglycaemia cost function being indicative of hypoglycaemia;

integrating the probabilities obtained during a selected time period comprising a plurality of time segments;

determining in said computer that the EEG signals are indicative of hypoglycaemia being present or being impending based on said integration; and in response to said determining step, providing an output notification of present or impending hypoglycaemia, wherein the method further comprises detecting artefact time segments from said plurality of time segments of said EEG, which contain signal contaminating artefacts, by obtaining a sum of a linear or non-linear function of the normalised features using a pre-established set of weighting coefficients to thereby obtain a time-varying artefact detection cost function, and classifying values of each said artefact detection cost function according to the probability of values of said artefact detection cost function being indicative of one of said artefacts; and excluding said artefact time segments from generating events to be included in said integration.

2. A method as claimed in claim 1, wherein said hypoglycaemia cost function is obtained as a sum of a linear or non-linear function of the normalised features using a pre-established set of weighting coefficients.

3. A method as claimed in claim 1, wherein the values of said hypoglycaemia cost function are classified as being an event indicative of hypoglycaemia or as being not an event indicative of hypoglycaemia, and said integration of probabilities is carried out by integrating the number of events detected during said selected time period.

4. A method as claimed in claim 1, further comprising estimating a long term mean of the hypoglycaemia cost function, estimating a long term variability of the hypoglycaemia cost function, and normalising the hypoglycaemia cost function by a process arithmetically equivalent to subtracting from the hypoglycaemia cost function the long term estimate of the mean of the hypoglycaemia cost function and dividing the result by the long term estimate of the variability of the hypoglycaemia cost function so as to generate the normalised hypoglycaemia cost function and wherein it is said normalised hypoglycaemia cost function which is classified in said classifying step.

5. A method as claimed in claim 1, further comprising estimating a long term mean of the artefact detection cost function, estimating a long term variability of the artefact detection cost function, and normalising the artefact detection cost function by a process arithmetically equivalent to subtracting from the artefact detection cost function the long term estimate of the mean of the artefact cost function and dividing the result by the long term estimate of the variability of the artefact cost function so as to generate the normalised artefact detection cost function and wherein it is said normalised artefact detection cost function which is classified in said classifying step.

6. A method as claimed in claim 1, wherein said measure of the intensities of said components is obtained for each of said plurality of time segments.

7. A method as claimed in claim 6, wherein said values of said hypoglycaemia cost function which are classified are values thereof for each of said plurality of time segments.

8. A method as claimed in claim 7, wherein said integration is carried out over a selected number of preceding time segments which together constitute said selected time period.

9. A method as claimed in claim 1, wherein a previous session estimate of the mean and variability is used at the start of a current session and is progressively updated as the current session progresses, and wherein a device used to implement the method has a nighttime and daytime mode, previous session estimates from a night time session are used to normalise intensity measures when the device is in the night time mode, and previous session estimates from a daytime session are used to normalise intensity measures when the device is in the daytime mode.

10. A method as claimed in claim 9, wherein a first set of pre-established weighting parameters is used when the system is in the night-time mode and a second set of pre-established weighting parameters is used when the system is in the daytime mode.

11. A method as claimed in claim 9, wherein the first set of weighting coefficients is determined by training on data collected during a night-time session and the second set of weighting coefficients is determined by training on data collected during a daytime session.

12. A method as claimed in claim 1, wherein said computer comprises a first processing unit coupled to receive said EEG signal and perform initial signal processing, and a second processing unit receiving processed signals transmitted from said first processing unit and performing further signal processing including said step of determining that the EEG signals are indicative of hypoglycaemia being present or impending.

13. A method as claimed in claim 12, wherein said first processing unit is an implanted unit.

14. A computer programmed to accept an EEG signal as an input and to perform thereon the steps of:
 obtaining from said EEG signal a plurality of components thereof each comprising a different band of frequencies;
 obtaining a measure of the varying intensity of each said component, obtaining a long term estimate of the mean of each said intensity measure and obtaining a long term estimate of the variability of each said intensity measure;
 normalising each said intensity measure by a process arithmetically equivalent to subtracting from the intensity measure the long term estimate of the mean and dividing the result by the long term estimate of the variability so as to generate from each frequency band a normalised feature;
 using machine analysis of the normalised features to obtain a time-varying hypoglycaemia cost function;
 classifying values of said hypoglycaemia cost function according to a probability of the values of said hypoglycaemia cost function being indicative of hypoglycaemia;
 integrating the probabilities obtained during a selected time period comprising a plurality of time segments, determining in said computer that the EEG signals are indicative of hypoglycaemia being present or being impending based on said integration;
 in response to said determining step, providing an output notification of present or impending hypoglycaemia, wherein a previous session estimate of the mean and variability is used at the start of a current session and is progressively updated as the current session progresses;
 detecting artefact time segments, from said plurality of time segments of said EEG, which contain signal contaminating artefacts by obtaining a sum of a linear or non-linear function of the normalised features using a pre-established set of weighting coefficients to thereby obtain a time-varying artefact detection cost function, and classifying values of each said artefact detection cost function according to the probability of values of said artefact detection cost function being indicative of one of said artefacts; and
 excluding said artefact time segments from generating events to be included in said integration.

15. A computer as claimed in claim 14, wherein said computer comprises a first processing unit coupled to receive said EEG signal and perform initial signal processing, and a second processing unit receiving processed signals transmitted from said first processing unit and performing further signal processing including said step of determining that the EEG signals are indicative of hypoglycaemia being present or impending.

16. A computer as claimed in claim 15, wherein said first processing unit is an implanted unit.

17. A non-transitory computer-readable medium carrying thereon a machine instruction set containing instructions for causing a compatible computer to carry out the step of receiving as an input an EEG signal and to perform thereon the steps of:
 obtaining from said EEG signal a plurality of components thereof each comprising a different band of frequencies;
 obtaining a measure of the varying intensity of each said component, obtaining a long term estimate of the mean of each said intensity measure and obtaining a long term estimate of the variability of each said intensity measure;
 normalising each said intensity measure by a process arithmetically equivalent to subtracting from the intensity measure the long term estimate of the mean and dividing the result by the long term estimate of the variability so as to generate from each frequency band a normalised feature;
 using machine analysis of the normalised features to obtain a time-varying hypoglycaemia cost function;
 classifying values of said hypoglycaemia cost function according to a probability of the values of said hypoglycaemia cost function being indicative of hypoglycaemia;
 integrating the probabilities obtained during a selected time period comprising a plurality of time segments, and determining in said computer that the EEG signals are indicative of hypoglycaemia being present or being impending based on said integration;
 in response to said determining step, providing an output notification of present or impending hypoglycaemia, wherein a previous session estimate of the mean and variability is used at the start of a current session and is progressively updated as the current session progresses;
 detecting artefact time segments, from said plurality of time segments of said EEG, which contain signal contaminating artefacts by obtaining a sum of a linear or non-linear function of the normalised features using a pre-established set of weighting coefficients to thereby obtain a time-varying artefact detection cost function, and classifying values of each said artefact detection cost function according to the probability of values of said artefact detection cost function being indicative of one of said artefacts; and
 excluding said artefact time segments from generating events to be included in said integration.

18. A wearable apparatus for detecting hypoglycaemia or impending hypoglycaemia by analysis of an EEG, said apparatus comprising one or more EEG measuring electrodes for gathering an EEG signal, a computer for receiving said EEG signals, said computer being programmed so as to carry out the steps of:
 obtaining from said EEG signal a plurality of components thereof, each component comprising a different band of frequencies;
 obtaining a measure of the varying intensity of each said component, obtaining a long term estimate of the mean of each said intensity measure and obtaining a long term estimate of the variability of each said intensity measure;

normalising each said intensity measure by a process arithmetically equivalent to subtracting from the intensity measure the long term estimate of the mean and dividing the result by the long term estimate of the variability so as to generate from each frequency band a normalised feature;

using machine analysis of the normalised features to obtain a time-varying hypoglycaemia cost function;

classifying values of said hypoglycaemia cost function according to a probability of the values of said hypoglycaemia cost function being indicative of hypoglycaemia;

integrating the probabilities obtained during a selected time period comprising a plurality of time segments, determining in said computer that the EEG signals are indicative of hypoglycaemia being present or being impending based on said integration;

in response to said determining step, providing an output notification of present or impending hypoglycaemia, wherein a previous session estimate of the mean and variability is used at the start of a current session and is progressively updated as the current session progresses;

detecting artefact time segments, from said pluraliy of time segments of said EEG, which contain signal contaminating artefacts confusable with hypoglycaemia patterns and excluding of a linear or non-linear function of the normalised features using a pre-established set of weighting coefficients to thereby obtain a time-varying artefact detection cost function, and classifying values of each said artefact detection cost function according to the probability of values of said artefact detection cost function being indicative of one of said artefacts; and excluding said artefact time segments from generating events to be included in said integration.

19. An apparatus as claimed in claim 18, wherein said computer comprises a first processing unit coupled to receive said EEG signals and perform initial signal processing, and a second processing unit receiving processed signals transmitted from said first processing unit and performing further signal processing including said step of determining that the EEG signals are indicative of hypoglycaemia being present or impending.

20. An apparatus as claimed in claim 19, wherein said first processing unit is an implanted unit.

* * * * *